United States Patent von Weissenfluh

[11] Patent Number: 5,195,889
[45] Date of Patent: Mar. 23, 1993

[54] DEVICE FOR THE RECONSTRUCTION OF AN ANGULAR ZONE OF A TOOTH

[75] Inventor: Beat von Weissenfluh, Gentilino, Switzerland

[73] Assignee: Hawe-Neos Dental Dr. H. Von Weissenfluh SA, Gentilino, Switzerland

[21] Appl. No.: 797,805

[22] Filed: Nov. 19, 1991

[30] Foreign Application Priority Data

Dec. 19, 1990 [CH] Switzerland .......................... 4025/90

[51] Int. Cl.$^5$ ............................................... A61C 9/00
[52] U.S. Cl. ...................................................... 433/40
[58] Field of Search ............................. 433/39, 40, 215

[56] References Cited

U.S. PATENT DOCUMENTS

| | | | |
|---|---|---|---|
| 3,357,104 | 12/1967 | Greene et al. | 433/40 X |
| 4,449,928 | 5/1984 | von Weissenfluh | 433/40 |
| 4,500,288 | 2/1985 | von Weissenfluh | 433/40 |
| 4,695,254 | 9/1987 | Herrell | 433/40 X |
| 4,824,365 | 4/1989 | von Weissenfluh | 433/40 |

FOREIGN PATENT DOCUMENTS

| | | | |
|---|---|---|---|
| 0087022 | 8/1983 | European Pat. Off. | 433/40 |
| 2599964 | 12/1987 | France | 433/40 |

*Primary Examiner*—Gene Mancene
*Assistant Examiner*—Nicholas D. Lucchesi
*Attorney, Agent, or Firm*—Young & Thompson

[57] ABSTRACT

A dental device includes an angular matrix (1), with a shape reproducing the shape of the zone of a tooth (3) on which an operation is performed. The matrix (1) is made of synthetic material transparent to light radiations used for photopolymerization of composite resins. Forceps (2), also similarly transparent, have ends (2',2") which, with the forceps (2) locked, form with their inside surfaces (2''',2$^{IV}$) a shape also substantially equal to that of the tooth (3). The matrices can be right or left and modeled for large incisors, small incisors or canine teeth. During the operation, the matrix (1) is kept in position simply by the lateral thrust exerted by the forceps (2) on a flap (1") extended along the contour of the matrix (1) and located substantially perpendicular to the matrix (1) itself.

6 Claims, 1 Drawing Sheet 5,195,889

DEVICE FOR THE RECONSTRUCTION OF AN ANGULAR ZONE OF A TOOTH

BACKGROUND OF THE INVENTION

The matrices now used for the reconstruction of angular made of aluminum alloys or of aluminum, exhibit two drawbacks. In the first place, the operation of "shaping" the matrix is laborious to make it correspond to the shape of the tooth on which the work is being performed: this operation is most often performed manually by the dentist, by making a plastic deformation of the matrix; in the second place, a fact still more disadvantageous, the matrices of aluminum or metals with similar mechanical characteristics necessarily cannot be transparent, and consequently preclude the use of photopolymerizable composite resins, which recently have increased their field of application thanks to the values and advantages they offer. But many matrices of transparent synthetic material in use today, while avoiding this latter drawback, comprise a very laborious intervention since the dentist has to hold them with his fingers in a suitable position to give a correct shaping to the resins used for the reconstruction, and at the same time to avoid shielding, with the fingers themselves, the radiations emitted by the lamps for photopolymerization of the said resins. Most of the time, this is a great problem.

Still there are also devices comprising forceps and an angular matrix of transparent material: generally two peduncles are applied on the two opposite sides of the matrix to hold the matrix in position, peduncles dimensioned to be able to be inserted in holes or notches made on the ends of forceps. But this solution also exhibits notable laboriousness and inconvenience due to the objective difficulty of keeping the forceps joined to the peduncles, exerting at the same time on the matrix the thrust, necessarily very delicate, suitable for keeping it in the desired position in the course of the operation.

SUMMARY OF THE INVENTION

The inventor has aimed, with the device of this application, to provide a functional, simple and economical solution able to eliminate the above-mentioned drawbacks completely.

The object of the invention is a dental device for the reconstruction of an angular zone of a tooth, comprising an angular matrix made of a material transparent to light radiations, able to cause the photopolymerization of the composite resins used for the reconstruction and externally carrying one or more projections and forceps for locking the matrix on the tooth on which the operation is being performed. The forceps also are made of a material transparent to said light radiations and have a shape suitable for allowing the connection to the projections to lock the matrix. The dental device is characterized by the fact that the projections are replaced by a flap being extended along the entire contour of the matrix and projecting substantially in the direction perpendicular to the inside surface of the matrix itself that adheres to the two walls of the tooth, so that the matrix is held in position by the lateral thrust exerted on it by the forceps.

BRIEF DESCRIPTION OF THE DRAWINGS

The functioning of the device will be described below with the accompanying drawings in which a preferred embodiment is illustrated. They show.

DETAILED DESCRIPTION OF THE PREFERRED EMBODIMENT

The device essentially comprises an angular matrix 1 and forceps 2 for its locking. Angular matrix 1 is made with a material transparent to light radiations suitable for causing photopolymerization of the composite resins used in dentistry for total or partial reconstruction of teeth.

The inside surface of this matrix 1, made, for example, by using molds and with one of the known processes used for drawing of plastic materials, has a shape substantially reproducing the shape of a tooth 3 on which it is to be applied.

For this purpose, right or left angular matrices are provided, i.e., suitable for being applied to the mesial or distal side of each tooth, and substantially reproducing the shape of a large incisor, of a small incisor or a canine tooth, i.e., the teeth that usually are the object of an angular reconstruction.

Figure 1:
in FIG. 1 the front view of a matrix that is part of the device of the invention.
Figure 2:
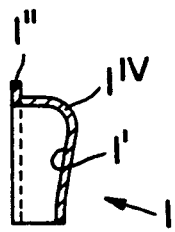
in FIG. 2, the view of its crosswise section made along line A—A.
Figure 3:
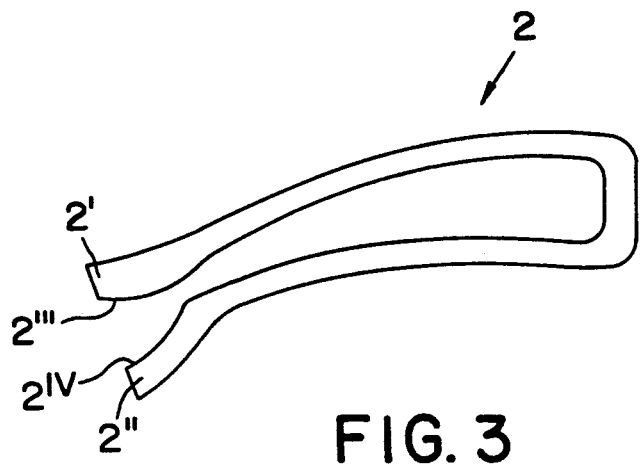
in FIG. 3, the side view of the forceps that are part of the device of the invention.
Figure 4:
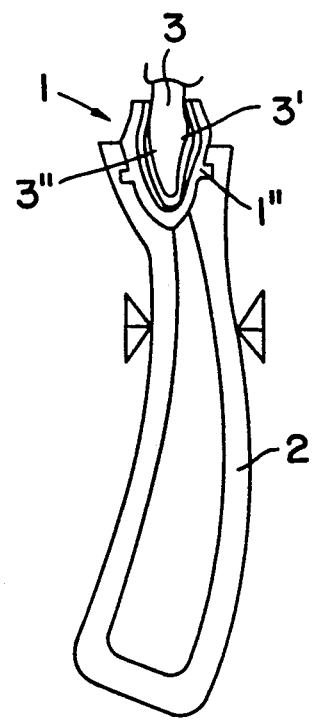
in FIG. 4, the side view of the device in the phase of its application to a tooth to be reconstructed.

The forceps 2, as seen in FIG. 3, are also made of a material having qualities of transparency similar to those cited for the matrix 1, but are further endowed with flexibility and resilience, and have their two ends 2', 2" dimensioned so that, when the forceps 2, are locked (in this connection see FIG. 4), inside surfaces 2''', $2^{IV}$ of the ends 2,40 , 2,41 themselves also form a shape substantially equal to that of the tooth 3 on which the operation is performed.

Existing angular matrices, as already said, externally exhibit one or more projections (peduncles) substantially perpendicular to the inside surface of the matrix 1, itself which adheres to the two walls of the tooth 3. These projections serve to prevent sliding of the forceps 2 relative to the matrix 1 and enable the forceps 2 to hold the matrix 1 pressed against the tooth 3 during the process.

But in the matrix 1 that is part of the device, these projections are replaced by a simple flap 1" extended along the entire contour of matrix 1. The forceps 2 exert a lateral pressure against the flap 1 during the operation, easily maintaining the matrix 1 in the desired position and without having to pay attention to maintaining the connection between the projections made in the ends 2', 2" of the forceps 2.

Thus, when the forceps 2 are locked on matrix 1 and the latter in turn is applied to the tooth 3, the resins, applied in the zone to be reconstructed and containing the matrix 1, are subjected to a "roughing" shaping, substantially assuming the shapes and contours of the parts of the tooth 3 to be reconstructed.

Then, it is possible to proceed to photopolymerization of the resins themselves by one of the lamps usually used for this purpose, then removing the matrix 1 when setting has occurred. The dentist will then have only to refine in detail the reconstructed zone according to the peculiar configuration of the tooth 3, after which the operation is finished.

The fact is indicated that the matrix 1 carries at least one hole $1^{IV}$ in the zone which, when the matrix 1 itself is applied on a tooth 3, is substantially opposite the apex of tooth 3 itself. This hole $1^{IV}$, with very limited diameter, is intended to avoid the formation of air bubbles inside the matrix 1 in the phase of filling it with the resins used for the reconstruction operation: in other words, the hole $1^{IV}$, allowing the escape of air from the matrix 1, makes it possible to perform a complete compaction of the matrix 1 itself, thus guaranteeing the obtaining of the appropriate shaping of the reconstructed zone.

The device, illustrated in the figures an described only according to a preferred embodiment, can be modified in the shape of the parts, in their relative dimensions and in the materials used, while always remaining within the scope of the concepts expressed herein. In the preferred embodiment are mentioned above, matrices 1 are made of polyester, and forceps 2 are made of polyester or polycarbonate.

I claim:

1. A dental device for reconstruction of an angular zone of a tooth (3), comprising:
    an angular matrix (1) made of a material transparent to light radiations able to cause photopolymerization of composite resins used for the reconstruction and externally carrying at least one projection;
    forceps (2) for locking the matrix (1) on the tooth (3) on which an operation is being performed;
    said forceps (2) being made of a material transparent to light radiations and having a shape suitable for allowing connection to said at least one projection to lock the matrix (1);
    characterized by the fact that said at least on projection is a flap (1") being extended along the entire contour of the matrix (1) and projecting outwardly of the matrix (1) that adheres to two walls (3', 3") of the tooth (3), so that the matrix (1) is held in position by lateral thrust exerted on it by the forceps (2);
    wherein the inside surface (1') of the matrix (1) has a shape substantially reproducing the shape of the tooth (3) on which it is to be applied and two ends (2', 2") of the forceps (2) are dimensioned so that, when the forceps (2) are locked, inside surfaces (241 40, $2^{IV}$ of) the ends (2', 2") themselves also form a shape substantially equal to that of the tooth (3); and
    wherein the matrix (1) carries at least one hole ($1^{IV}$) in a zone which, when the matrix (1) is applied on the tooth (3), is substantially opposite an apex of the tooth (3) itself.

2. Device according to claim 1, wherein the shape of the inside surface (1') of the matrix (1) reproduces a shape of a large incisor tooth at its mesial or distal side.

3. Device according to claim 1, wherein the shape of the inside surface (1') of the matrix (1) reproduces a shape of a small incisor tooth at its mesial or distal side.

4. Device according to claim 1, wherein the shape of the inside surface (1') of the matrix (1) reproduces a shape of a canine tooth at its mesial or distal side.

5. Device according to claim 1, wherein the both the matrix (1) and the forceps (2) are made of synthetic material.

6. Device according to claim 5, wherein the matrix (1) itself is made of polyester and the forceps (2) are made of either polyester or polycarbonate.

* * * * *